United States Patent
Kaspar et al.

(10) Patent No.: US 9,789,122 B2
(45) Date of Patent: Oct. 17, 2017

(54) HORMONE CONTAINING EMULSION

(71) Applicant: B. Braun Melsungen AG, Melsungen (DE)

(72) Inventors: Ilona Kaspar, Phillipsthal (DE); Volker Krüger, Nieste (DE); Doris Röthlein, Kassel (DE); Martin Wolf, Melsungen (DE); Jürgen Schmitt, Kirchhain (DE)

(73) Assignee: B. Braun Melsungen AS, Melsungen (DE)

( * ) Notice: Subject to any disclaimer, the term of this patent is extended or adjusted under 35 U.S.C. 154(b) by 0 days.

(21) Appl. No.: 14/379,505

(22) PCT Filed: Feb. 25, 2013

(86) PCT No.: PCT/EP2013/053686
§ 371 (c)(1),
(2) Date: Aug. 19, 2014

(87) PCT Pub. No.: WO2013/127728
PCT Pub. Date: Sep. 6, 2013

(65) Prior Publication Data
US 2015/0011515 A1 Jan. 8, 2015

(30) Foreign Application Priority Data

Feb. 29, 2012 (EP) ..................... 12157546

(51) Int. Cl.
A61K 31/57 (2006.01)
A61K 31/565 (2006.01)
A61K 47/44 (2006.01)
A61K 9/107 (2006.01)
A61K 31/573 (2006.01)
A61K 9/00 (2006.01)
A61K 47/14 (2017.01)
A61K 47/24 (2006.01)

(52) U.S. Cl.
CPC .......... *A61K 31/573* (2013.01); *A61K 9/0019* (2013.01); *A61K 9/107* (2013.01); *A61K 9/1075* (2013.01); *A61K 31/565* (2013.01); *A61K 31/57* (2013.01); *A61K 47/14* (2013.01); *A61K 47/24* (2013.01); *A61K 47/44* (2013.01)

(58) Field of Classification Search
IPC ..................... A61K 31/37,31/565, 47/44, 9/107
See application file for complete search history.

(56) References Cited

U.S. PATENT DOCUMENTS

| | | | |
|---|---|---|---|
| 8,241,672 B2 * | 8/2012 | Driscoll | A23D 7/003 424/523 |
| 8,476,252 B2 | 7/2013 | Achleitner et al. | |
| 8,586,078 B2 | 11/2013 | Faure et al. | |
| 8,729,124 B2 | 5/2014 | Calder et al. | |
| 8,765,149 B2 | 7/2014 | Achleitner et al. | |
| 2006/0067952 A1 * | 3/2006 | Chen | A61K 9/0019 424/400 |
| 2007/0071777 A1 | 3/2007 | Bromer et al. | |
| 2010/0173876 A1 | 7/2010 | Lichtenberger et al. | |
| 2012/0321720 A1 * | 12/2012 | Driscoll | A61K 31/6615 424/522 |

FOREIGN PATENT DOCUMENTS

| | | | |
|---|---|---|---|
| EP | 1488785 | * | 6/2003 |
| RU | 2009 145 010 A | | 6/2011 |
| WO | WO 2005/037848 A2 | | 4/2005 |
| WO | WO 2006102596 A2 | | 9/2006 |
| WO | WO 2006102596 A3 | | 9/2006 |
| WO | WO 2006102644 A2 | | 9/2006 |
| WO | WO 2006102644 A3 | | 9/2006 |
| WO | WO 2007080515 A1 | | 7/2007 |
| WO | WO 2008039898 A2 | | 4/2008 |
| WO | WO 2008039898 A3 | | 4/2008 |
| WO | WO 2010/104575 A2 | | 9/2010 |
| WO | WO 2011/134944 A2 | | 11/2011 |

OTHER PUBLICATIONS

Gras (2002) and further in view of Lemerond (2008).*
Lemerond(2008).Lemerond (2008).*
Abstract of Chinese Patent—CN101152186, Apr. 2, 2008, 1 page.
Abstract of Japanese Patent—JPS60258110, Dec. 20, 1985, 1 page.
Abstract of WO Patent—WO2004110402, Dec. 23, 2004, 1 page.
Article—Aklayed at al., "Neuroprotective Effects of Female Gonadal Steroids in Reproductively Senescent Female Rats," *Stroke*, vol. 31, 2000. pp. 161-168.
Article—Wright et al, "ProTECT: A Randomized Clinicai Trial of Progesterone for Acute Traumatic Brain Injury," *Annals of Emergency Medicine*, vol. 49, No. 4, Apr. 2007, pp. 391-402.
Article—Xiao et al, "Improved outcomes from the administration of progesterone for patients with acute severe traumatic brain injury: a randomized controlled trial," *Critical Care*, vol. 12, Issue 2, 2008, 10 pages.
International Search Report for PCT/EP2013/053686 dated Jun. 11, 2013, 3 pages.
Abstract and Machine Translation of CN102277237, Dec. 14, 2011, (abstract 1 page) (translation 5 pages).
Article—YING-XIANG, C., "Research on Fish Oil Concentration and Powdering Technology," *China Academic Journal*, vol. 21, No. 6, 2000, pp. 33-37.
Abstract of Chinese Patent—CN102277237 dated Dec. 14, 2011, 1 page.
Taiwanese Search Report for TW Application No. 102106873, 1 page.
Abstract of Japanese Patent—JP2006527736A, dated Dec. 7 2006, 1 page.
Abstract of Japanese Patent—JP2007291078A, dated Nov. 8, 2007, 1 page.
Bailes et al., "Docosahexaenoic Acid Reduces Traumatic Axonal Injury in a Rodent Head Injury Model," Journal of Neurotrauma, vol. 27, No. 9, Sep. 2010, pp. 1617-1624, 8 pages.

(Continued)

*Primary Examiner* — Shirley V Gembeh
(74) *Attorney, Agent, or Firm* — Dority & Manning, P.A.

(57) ABSTRACT

The present invention relates to a hormone containing oil-in-water emulsion for parenteral administration comprising a) progestogen and/or estrogen and b) fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty acids.

11 Claims, 2 Drawing Sheets

(56) References Cited

OTHER PUBLICATIONS

Figure 1:
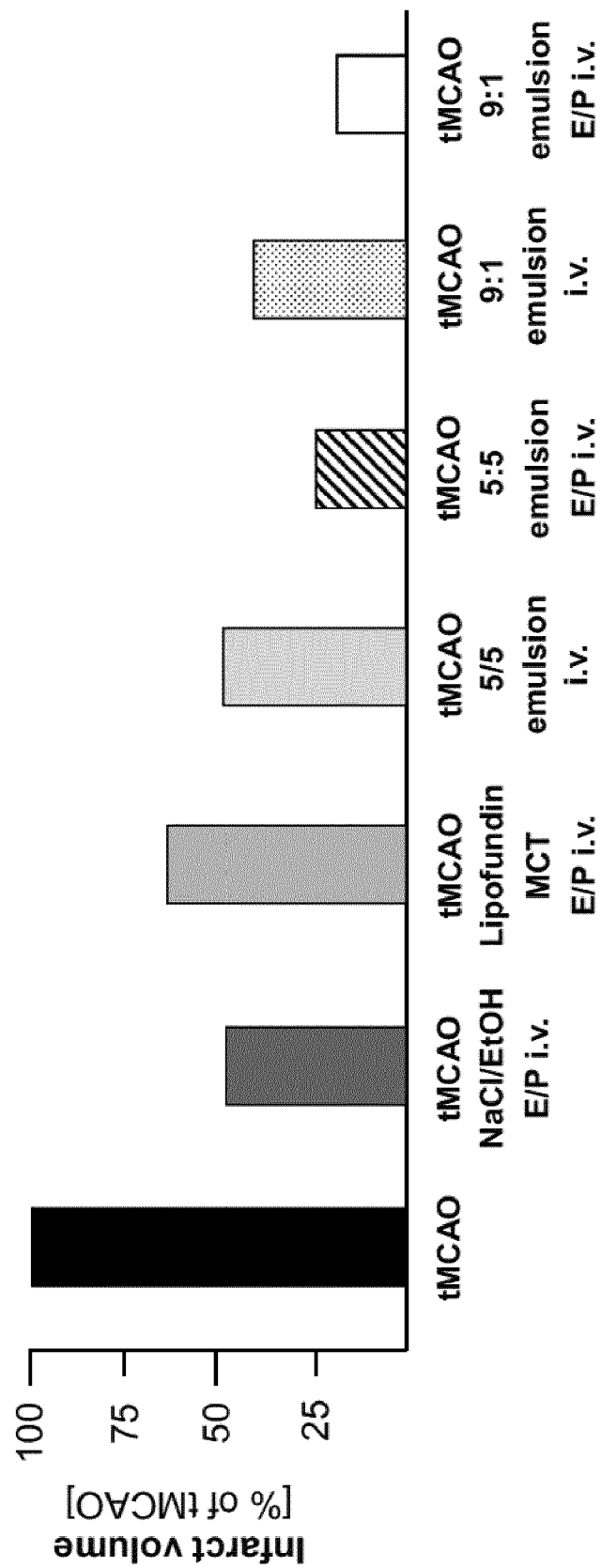

Dyall et al., "Neurological Benefits of Omega-3 Fatty Acids," Neuromal Med., vol. 10, No. 4, 2008, pp. 219-235, 17 pages.

Kipp et al., "Sex Steroids Control Neuroinflammatory Processes in the Brain: Relevance for Acute Ischaemia and Degenerative Demyelination," Journal of Neuroendocrinolgy, vol. 24, No. 1, 2012, pp. 62-70, 9 pages.

Singh et al., "Estrogens and Progesterone as Neuroprotectants: What Animal Models Teach Us," Front Biosci, Author manuscript, vol. 13, 2008, 12 pages.

\* cited by examiner

HORMONE CONTAINING EMULSION

CROSS REFERENCE TO RELATED APPLICATIONS

This application is the national stage entry of International Patent Application No. PCT/EP2013/053686 having a filing date of Feb. 25, 2013, which claims priority to and the benefit of European Patent Application No. 12157546.8 filed in the European Patent Office on Feb. 29, 2012, the entire contents of which are incorporated herein by reference.

The invention relates to hormone containing oil-in-water emulsion for parenteral administration comprising progestogen and/or estrogen; and fish oil triglycerides as well as a pharmaceutical composition comprising or consisting of said oil-in-water emulsion. The pharmaceutical composition is especially for use in the treatment or prophylaxis of neurological damage after strokes and/or trauma and/or for use in the treatment or prophylaxis of neurological damage after concussion and/or traumatic injury to the central nervous system.

BACKGROUND

Traumatic Brain Injury (TBI) is a non-degenerative, non-congenital insult to the brain from an external mechanical force, possibly leading to permanent or temporary impairments of cognitive, physical and psychosocial functions with an associated diminished or altered state of consciousness. Some patients have a long-term or lifelong need for help to perform activities of daily living as a result of TBI.

Despite the enormity of the problem posed by TBI, there are currently no approved medications proven to be effective in improving mortality or in improving outcomes following TBI. However, two recent clinical trials have demonstrated successful treatment of TBI with the steroid hormone progesterone (Xiao et al, 2008, Crit. Care, 12: R61; Wright et al Ann. Emerg. Med. 2007, 49: 391-402). Both studies showed that progesterone is safe and well tolerated in TBI patients, and that administration of progesterone to TBI patients leads to decreased mortality. Furthermore, patent applications WO2006/102644, WO2006102596, WO2008/039898, US 2011/0262494 and US 2011/0262495 outline methods for treatment of TBI by parenterally administering progestogen.

Further, Alkayed et al. in Stroke 31, 161 (2003) describe the positive influence of subcutaneously administered estrogens and progesterones on the condition of stroke patients.

A stroke, also known as a cerebrovascular accident (CVA), is the rapid loss of brain function(s) due to disturbance in the blood supply to the brain. This can be due to ischemia (lack of blood flow) caused by blockage (thrombosis, arterial embolism), or a hemorrhage (leakage of blood). As a result, the affected area of the brain cannot function, which might result in an inability to move one or more limbs on one side of the body, inability to understand or formulate speech, or an inability to see one side of the visual field.

A stroke is a medical emergency and can cause permanent neurological damage, complications, and death. It is the leading cause of adult disability in the United States and Europe and the second leading cause of death worldwide. Risk factors for stroke include old age, hypertension (high blood pressure), previous stroke or transient ischemic attack (TIA), diabetes, high cholesterol, cigarette smoking and atrial fibrillation. High blood pressure is the most important modifiable risk factor of stroke.

The most effective route of administration of progestogens such as progesterone and/or estrogen such as estradiol is via parenteral such as intravenous administration. However, the hydrophobic nature of the progesterone and/or estradiol molecules, and hence its poor solubility in water, presents formulation limitations. Aqueous solutions do not offer formulations capable of delivering effective therapeutic doses of progesterone to patients. However, progesterone and/or estradiol is sufficiently lipophilic to enable therapeutically effective concentrations to be prepared in hydrophobic solvents, such as triglyceride based solvents.

The delivery of hydrophobic drugs via intravenous infusion of oil-in-water emulsions is known in the art. In Wright et al., Ann. Emerg. Med. 2007, 49: 391-402 a 2-component system is utilized, wherein progesterone is firstly dissolved in an alcoholic solution (first component), and this alcoholic progesterone solution is subsequently injected into the commercially available lipid emulsion Intralipid® 20% (Fresenius Kabi, Sweden) (second component), and manually mixed (such as by shaking) shortly before intravenous administration of the alcoholic solution/emulsion mixture. There are multiple disadvantages of using this method of preparation:

Firstly, administration of alcoholic solutions to TBI patients is not desirable. Secondly, whilst the presence of alcohol aids solubilization of the progesterone and/or estradiol, low shear manual mixing does not enable all of the progesterone/estradiol to enter the oil phase. Consequently such emulsions are capable of solubilising only a limited amount of progesterone or estradiol, and large amounts of lipid must therefore be administered in order to achieve the desired serum-progesterone and/or estrogen levels. However, administration of large volumes of emulsion, and/or large amounts of lipid to the patient can have serious consequences, such as induction of hyperlipidemia or oedema. The patient is, as a result, exposed to an undesirable lipid and/or liquid load and is placed at risk of adverse reactions.

Furthermore, non-dissolved progestogen and/or estrogen is susceptible to crystallization, and subsequently oxidation in the aqueous phase, thus causing not only elevated levels of particulate matter to accumulate in the composition, but also high levels of degradation products of the active ingredient. Indeed, it has been shown that, when an alcoholic solution of progesterone is injected into a commercial lipid emulsion composition (such as Intralipid® 20%), a fraction of the hormone is found in crystalline form rather than becoming solubilised in the emulsion. This non-solubilised progesterone has been reported to be adsorbed at the surface of the infusion bags and feed ducts. The observation that not all of the progesterone enters the oil phase of these 2-component emulsions leads to uncertainty as to the concentration of progesterone achieved in the final composition, and the bio-availability of the hormone.

Finally, due to stability issues, the progesterone-lipid mixture of 2-component systems must be prepared only hours ahead of administration (i.e. the first component is added to the second component and mixed within hours of use), as the resulting mixture may not be stored at room temperature. It is both time consuming and inconvenient for medical practitioners to prepare such mixtures on demand, and particularly unsatisfactory in the context of TBI therapy, where prompt treatment can be important to patient outcome.

Alternative methods for making hormone-containing emulsions describe the incorporation of hormone directly into the oil during manufacture of the lipid emulsion (WO 2004/110402).

CN 101152186 describes the use of the surfactants Solutol S15 or poloxamer 188 in the preparation of injectable progesterone formulations. Whilst use of these surfactants may achieve a high progesterone solubility, intravenous administration of high concentrations of these surfactants is associated with undesirable side-effects including moderate elevation in histamine release, urticaria, and anaphylactic reactions (pruritis, erythema).

One method of increasing the solubility of progesterone and/or estradiol in lipid emulsions known in the art is the use of organic solvents. Progesterone is highly soluble in benzoic acid or its derivatives. For example, JP 60-258110 describes the use of benzyl benzoate to increase progesterone solubility in a lipid emulsion. However, since benzyl alcohols and benzyl benzoate are commonly toxic and are known to elicit allergies, their inclusion in compositions for parenteral administration is considered a serious danger.

Independent from the problems associated with the solubility and the stability of the emulsions there remains the problem to improve the effectivity of the hormones in the treatment or prophylaxis of neurological damages.

It has been surprisingly found that the problems associated with the prior art can be solved by a hormone containing oil-in-water emulsion for parenteral administration comprising progestogen and/or estrogen; and an omega-3-fatty acid enriched fish oil and/or phospholipids comprising one or more omega-3-fatty acid moieties.

DEFINITIONS

The term "oil" as used herein is readily interchangeable with "lipid" and "fat", and refers to lipophilic high-boiling organic compounds that are liquid at body temperatures, (e.g. about 37° C.), and are pharmacologically acceptable in injectable formulations. The oils of the present invention encompass both glycerides, partial glycerides, fatty acid residues and non-glycerides as well as mixtures thereof. Phospholipids, unless otherwise indicated, are not encompassed by the term "oil" as used herein.

The term "oil-in-water emulsion" as used herein, refers to a colloidal dispersion system in which liquid oil is dispersed in small droplets (the discrete phase) in an aqueous medium (the continuous phase).

The term "phospholipid" as used herein refers an ester of glycerol with one or two fatty acids and one phosphate group. In addition to glycerol-derived phopholipids, the term "phospholipid" as used herein also encompasses sphingomyelin.

The term "aqueous medium" as used herein refers to a water-containing liquid.

As used herein, the singular forms "a", "an" and "the" designate both the singular and the plural, unless expressly stated to designate the singular only.

As used herein, the phrase "therapeutically effective amount" means that drug dosage that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

Unless indicated otherwise, whenever reference is made herein to "percentage weight per volume" or "% wt/vol" these terms describe the mass of the component in g per 100 mL of the composition in which it is contained. Unless indicated otherwise, whenever reference is made herein to "percentage weight per weight" or "% wt/wt" these terms denote the mass of a component as a percentage of the mass of the composition in which the component is contained.

Whenever "PCS" or "Photon Correlation Spectroscopy" is referred to herein, what is meant is PCS as measured according to the method described in USP, Chapter <729>, Method I, using the Zetasizer 1000 HSA (Malvern Instruments).

Whenever d(0,5) (volume-based mean diameter) is referred to herein, what is meant is d(0,5), measured according to the method described in USP <429> (Light diffraction measurement of particle size), using the Mastersizer 2000 with Hydro S dispersion unit (Malvern Instruments).

Whenever "zeta-potential" is referred to herein, what is meant is the electrokinetic potential in colloidal systems as determined experimentally using Zetasizer 1000 HAS (Malvern Instruments).

Whenever the term "free of crystalline solid" is used herein, it is meant that emulsions of the present invention meet the standards for particulate size and count in injection liquids (USP 788, Method 2-Microscopic Particle count test).

DETAILED DESCRIPTION

A first embodiment of the present invention is a hormone containing oil-in-water emulsion for parenteral administration comprising
a) progestogen and/or estrogen and
b) fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty.

The oil-in-water emulsion of the present invention comprises an oil and an aqueous phase.

The oil-in-water emulsion of the present invention comprises a progestogen and/or estrogen as the active pharmaceutical ingredient (API).

As used herein, "progestogen" includes both natural progesterone and synthetic progestogens. In general, the progestogens have the general Formula I, wherein X1 and X2 are independently selected from —COCH$_3$, —OCOC$_5$H$_{11}$, —OH, ethinyl, —OCOCH$_3$, —H, —CH$_2$CN; wherein X3 is selected from —H, —CH$_3$, or —Cl; wherein X4 is selected from —H, —OH, or —CH$_3$, and wherein X5 is selected from CH$_3$ or CH$_2$CH$_3$. The progestogen may contain ring structures with one of more double bonds, for example between carbons 3 and 4, 4 and 5, 5 and 6, 6 and 7, 5 and 10, 10 and 9, and/or 15 and 16.

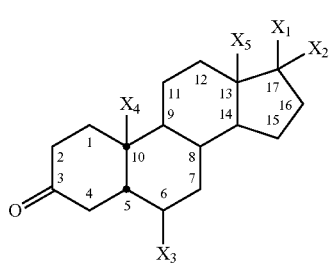

Formula I

Such progestogens include, for example, derivatives of progesterone such as 5-α-dihydroprogesterone, 6-dehydro-retroprogesterone (dydrogesterone), hydroxyprogesterone caproate, levonorgestrel, norethindrone, norethindrone acetate; norethynodrel, norgestrel, medroxyprogesterone, chlormadinone, and megestrol. "Progestogen" also includes, but is not limited to modifications that produce 17α-OH esters of progesterone, as well as, modifications that introduce 6-α-methyl, 6-methyl, 6-ene, and 6-chloro substituents onto progesterone, and/or 19-nor-progesterones. Further, non-limiting examples, of synthetic progestogens include, norethindrone (Micronor®), norgestrel (Ovrette®), levonorgestrel (Norplant®; with ethinyl estradiol; Alesse®, Nordette®), gestodene, medroxyprogesterone acetate (Provera®), promegestone, nomegestrol acetate, lynestrenol and dienogest.

In one embodiment, the progestogen is selected from the group consisting of progesterone, norethynodrel, norethidrone acetate, medroxyprogesterone, medroxyprogesteron 17-acetate, levonorgestrel, dydrogesterone, hydroxyprogesterone caproate, norethidrone, gestodene, nomegestrol acetate, promegestone, dienogest, chlormadinion, megestrol, megestrol acetate, and/or mixtures thereof.

In specific embodiments, the progestogen is selected from the group consisting of 5-α-dihydroprogesterone, medroxyprogesterone, dydrogesterone, and progesterone and/or mixtures thereof.

In a further embodiment the progestogen is selected from the group consisting of pregnelonone, progesterone, medroxyprogesterone and their pharmaceutically acceptable derivatives.

In specific embodiments, the progestogen is progesterone. The term "progesterone" as used herein refers to a member of the progestogen family having the structure of Formula II below:

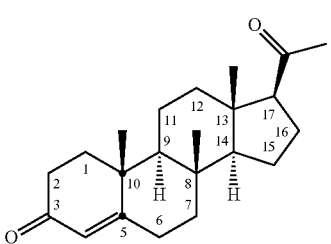

Formula II

Progesterone is also known as D4-pregnene-3,20-dione; delta-4-pregnene-3,20-dione; or pregn-4-ene-3,20-dione. In very specific embodiments the progesterone is micronized. Proquina (Mexico) is one supplier of micronized progesterone.

The progestogen (e.g., any progestogen, including progesterone) which is suitable for use in accordance with the present invention may be in the form of a pharmaceutically acceptable salt.

The oil-in-water emulsion of the invention may comprise an amount of progestogen of at least 0.1 g/l, preferably at least 0.15 g/l, more preferably ranging from 0.15 g/l to 12.0 g/l, further preferably 0.8 g/l to 4.0 g/l, especially 1.0 g/l to 2.5 g/l.

In a preferred embodiment the oil-in-water emulsion comprises progesterone in an amount ranging from 0.15 g/l to 12 g/l.

The oil-in-water emulsion of the present invention may comprise an amount of progestogen (e.g., progesterone) of at least 0.3 g/l, at least 0.5 g/l, at least 1 g/l. In accordance with any of these embodiments, the emulsion may comprise an amount of progestogen (e.g., progesterone) less than or equal to 3.0 g/l, less than or equal to 2.5 g/l, or less than or equal to 2.0 g/l. In a particular embodiment, the oil-in-water emulsion of the invention comprises about 1.0 g/l to 2.0 g/l of progesterone, specifically about 1.5 g/l progesterone.

According to an alternative embodiment of the invention the oil-in-water emulsion comprises one or more estrogens.

In a preferred embodiment the emulsion comprises estriol (1,3,5(10)-estratriene-3,16α,17β-triol) which is reflected in formula III below:

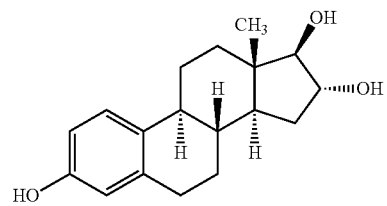

Formula III

In a further embodiment the emulsion comprises estradiol (1,3,5(10)-estratriene-3,17β-diol) which is reflected in Formula IV below:

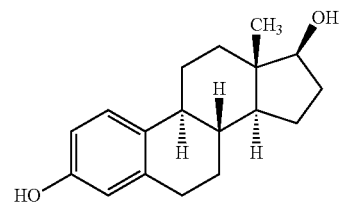

Formula IV

In a further embodiment the emulsion comprises estrone which is reflected in Formula V below:

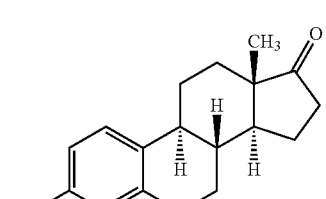

Formula V

According to a preferred embodiment of the invention the oil-in-water emulsion comprises estrogens selected from the group consisting of estradiol, estrone, esttriol and derivatives as well as mixtures thereof.

Specifically preferred is estradiol.

The estrogens are preferably present in the oil-in-water emulsion in an amount ranging from 0.015 g/l to 5 g/l, more preferably 0.015 g/l to 1.5 g/l and most preferably from 0.05 g/l to 0.3 g/l (gram per liter), based on the emulsion.

In a preferred embodiment the emulsion comprises estradiol in an amount ranging from 0.015 g/l to 1.5 g/l, preferably 0.05 g/l to 1.0 g/l, more preferably 0.08 g/l to 0.5 g/l and especially 0.1 g/l to 0.3 g/l.

According to a further embodiment of the present invention the oil-in-water emulsion comprises a combination of progestogen and estrogen. The weight ratio of progestogen to estrogen in the emulsion may be from 2:1 to 500:1, preferably 2:1 to 200:1, further preferably from 5:1 to 50:1 and more preferably from 10:1 to 20:1.

Preferably, the oil-in-water emulsion comprises estradiol and/or progesterone.

One embodiment of the invention relates to the combination of estrone with pregnelonone and/or progesterone, another to the combination of estriol with pregnelonone and/or progesterone. An alternative, particularly preferred embodiment relates to the combination of estradiol and/or pregnelonone and/or progesterone, especially with progesterone. In both alternatives, medroxyprogesterone may be additionally contained, or medroxyprogesterone may be substituted for pregnelonone and/or progesterone. Thus, more than two hormones may also be combined according to the invention.

For a better dosing of the oil-in-water emulsions, the parent emulsions can be diluted, if necessary, with an appropriate amount of water, preferably with up to the fourfold amount of water.

The oil phase of the oil-in-water emulsion comprises fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty acids and preferably the total amount of omega-3-fatty acids is at least 50% by weight (wt.-%), more preferably at least 55 wt.-%, more preferably at least 60 wt.-% and most preferably at least 65 wt.-% of said fatty acids.

In the European Pharmacopeia (EP), there are two monographs (i.e., EP 1352 entitled "Omega-3 Acid Triglycerides", and, EP 1912 entitled "Fish Oil, Rich in Omega-3 Acids") that pertain to fish oil that is acceptable for use in parenteral emulsions (EP 1352, EP 1912, 2008). The monograph EP 1352 substantially differs from EP 1912 in that the composition and requirements for the bioactive n3-FAs in EP 1352 are much higher than in EP 1912 (EP 1352: EPA+DHA≥45%; total n3-FAs 60% vs. EP 1912: EPA: 13%; DHA 9%; total n3-FAs≥28%). The levels of n3-FAs in EP 1912 are consistent with those found in nature. By comparison, in EP 1352, the n3-FA concentrations are substantially higher and can be obtained by an enrichment process such as molecular distillation, whereby certain undesirable fatty acids that are present, for example, myristic acid, palmitic acid and stearic acid, are removed. In so doing, the concentrations of all fatty acids present, and particularly the omega-3 fatty acids, are proportionately elevated. In an exemplary embodiment, the fish oil triglycerides include omega-3 fatty acids in an amount of at least 60%, preferably at least 65% by weight, based on the total weight of the fatty acids of the fish oil triglycerides. The fish oil triglycerides include a total amount of eicosapentaenoic acid (EPA) and docosahexaenoic acid (DHA) of at least 45%, preferably at least 50% by weight, based on the total weight of the fatty acids of the fish oil triglycerides. For example, the fatty acids and omega-3 fatty acids (such as, for example, EPA and DHA) discussed herein refer to the constituent parts of such acids in a fish oil triglyceride, in accordance with EP 1352. For example, the fatty acids and omega-3 fatty acids (such as, for example, EPA and DHA) discussed are in their esterified form when present in the fish oil triglycerides.

According to the invention the fish oil triglycerides comprise omega-3-fatty acids composed of eicosapentaenoic acid in an amount of 30% or greater, docosahexaenoic acid in an amount of 30% or less, and docosapentaenoic acid in an amount of about 40% or less, based on the weight of the total omega-3 fatty acid content.

The fish oil triglycerides can contain at least one omega-6 fatty acid, for example, a plurality of omega-6 fatty acids. The at least one omega-6 fatty acid can include, for example, arachidonic acid or AA (20:4n6), linoleic acid or LA (18:2n6), gamma linolenic acid or ALA (18:3n6) or a combination thereof. For example, the total content of the at least one omega-6 fatty acid can be from about 0.1% to about 1.0%, or from about 0.2% to about 0.9%, or from about 0.3% to about 0.8%, or from about 0.4% to about 0.7%, or from about 0.5% to about 0.6%, based on the weight of the fatty acids which are esterified with glycerol to form the fish oil triglyceride.

Determination of the content of the omega-3 fatty acids (n3-FAs) can be made as described in the European Pharmacopeia "Fish oil, rich in omega-3 acids". The content of n3-FAs can be from any single n3-FA, or any combination thereof. In an exemplary embodiment, the composition can contain EPA, DHA, DPA or a combination thereof, for example, each of EPA, DHA and DPA. The individual dosage, for example total daily dosage, of eicosapentaenoic acid (EPA) can vary from 0 to 300 mg/kg of the formulation, for example, from 50 to 250 mg/kg, for example, from 100 to 200 mg/kg, based on the body weight. The individual dosage, for example total daily dosage, of docosahexaenoic acid (DHA) can vary from 0 to 300 mg/kg of the formulation, for example, from 50 to 250 mg/kg, for example, from 100 to 200 mg/kg, based on the body weight. The individual dosage, for example total daily dosage, of docosapentaenoic acid (DPA) can vary from 0 to 300 mg/kg of the formulation, for example, from 50 to 250 mg/kg, for example, from 100 to 200 mg/kg, based on the body weight. For example, EPA, DHA and/or DPA can be present in amounts which are effective to provide neuro protection to vital organs.

The fish oil triglycerides may be present in an amount of at least 25 wt.-%, preferably at least 35 wt.-%, further preferably at least 50 wt.-%, especially at least 75 wt.-% and particularly at least 85 wt.-%, each based on the total weight of the oil component.

According to a preferred embodiment the fish oil triglycerides are present in an amount ranging from 55 to 95 wt.-%, more preferably 60 to 92 wt.-%, especially 70 to 90 wt.-%, based on the total weight of the oil component.

According to a preferred embodiment of the invention the oil-in-water emulsion additionally comprises medium chain triglycerides (MCT).

An exemplary second component of the oil component of the emulsion can include at least one medium chain triglyceride (MCT), for example, a plurality of MCTs. For example, the at least one MCT can be present from about 10% to about 69%, or from about 10% to about 40%, or from about 10% to about 30%, or from about 10% to about 20%, or from about 10% to about 15%, or from about 20% to about 60%, or from about 30% to about 50%, or from about 40% to about 45%, based on the total weight of the oil component of the emulsion. For example, by employing exemplary ranges of MCT, the amount of esterified omega-3 fatty acids delivered to a human body can be increased. For example, by employing exemplary MCT ranges, the amount of esterified omega-3 fatty acids delivered to a human body can be increased with usage of a relatively smaller amount of MCT, while still achieving beneficial metabolic clearance and physicochemical stability characteristics of the emulsion.

For example, the MCT can include a saturated medium chain fatty acid, for example, a plurality of saturated medium chain fatty acids. In an exemplary embodiment, the MCT is a triglyceride of a fatty acid having from 6 to 12 carbon atoms. The MCT can be derived from a plant such as a vegetable, for example, a plurality of plants. The MCT can contain caprylic acid (for example, in an amount of about 50% to about 80% by weight of the MCT), an 8-carbon saturated FA (8:0). The MCT can contain capric acid (for example, in an amount of about 20% to about 50% by weight of the MCT), a 10-carbon saturated FA (10:0). For example, the medium-chain triglycerides can contain triglycerides of caprylic acid and capric acid, in an amount of at least 90% by weight of the medium-chain triglycerides. The description of the MCT for use in this disclosure can, for example, meet the requirements of EP monograph 0868, entitled "Triglycerides, Medium Chain" (Triglycerida saturate media) (EP 0868, 2008).

The oil of the oil-in-water emulsion compositions described herein may additionally comprise medium chain triglycerides. "Medium chain triglycerides" (MCTs) are another class of triglyceride oil that can be either naturally derived or synthetic. MCTs are formed from fatty acids of 6 to 14 carbons, preferably 6 to 12 carbons, especially 8 to 10 carbons, in length. The medium-chain triglycerides (MCT) administered with the oil-in-water emulsions predominantly serve as an energy source. MCT is commercially available as for example Miglyol 812 (SASOL GmbH Germany), or CRODAMOL GTCC-PN (Croda Inc, New Jersey).

According to an preferred embodiment of the present invention the emulsion comprises an MCT which is consisting of glycerol which is esterified with fatty acids comprising at least 50 wt.-% of fatty acids selected from the group of fatty acids having 7, 9 and 11 carbon atoms.

The combination of MCT with the fish oil triglycerides as defined above are of advantage for the oil-in-water emulsions of the present invention.

According to a preferred embodiment of the present invention the oil-in-water emulsion comprises medium chain triglycerides in an amount ranging from 5 to 75 wt.-%, preferably from 10 to 55 wt.-% and especially from 15 to 45 wt.-%, each based on the total weight of the oil component.

In a preferred embodiment of the invention the oil in water emulsion comprises the fish oil triglycerides and medium chain triglycerides in a weight ratio ranging from 1:1 to 9:1, more preferably 1.5:1 to 8:1, especially 2:1 to 7:1.

According to a especially preferred embodiment the amount of fish oil triglycerides and MCT in the oil phase is at least 90 wt.-%, preferably at least 95 wt.-%, more preferably at least 98 wt.-%, especially at least 99 wt.-%, based on the total weight of the oil component.

The oil component may additionally comprise further oils, which preferably have a melting point of less than 30° C., more specifically of less than 20° C., and including less than 10° C.

Preferably the oil component contains oil comprising at least 75 wt.-% triglycerides, or at least 85 wt.-% triglycerides, based on the total weight of the oil component. In a specific embodiment the oil component comprises at least 90 wt.-% triglycerides, or at least 95 wt.-% triglycerides.

In further specific embodiments, the oil phase additionally comprises "long-chain triglycerides" (LCT).

In certain embodiments the oil may comprise a vegetable oil. "Vegetable oil" refers to oil derived from plant seeds or nuts. Vegetable oils are typically "long-chain triglycerides" (LCTs), formed when three fatty acids (usually 14 to 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are used to ensure safety and stability of the oil-in-water emulsions. In certain embodiments hydrogenated vegetable oils, which are produced by controlled hydrogenation of the vegetable oil, may be used.

Exemplary vegetable oils include but are not limited to almond oil, babassu oil, black currant seed oil, borage oil, canola oil, caster oil, coconut oil, corn oil, cottonseed oil, olive oil, peanut oil, palm oil, palm kernel oil, rapeseed oil, safflower oil, soybean oil, sunflower oil and sesame oil. Hydrogenated and/or or partially hydrogenated forms of these oils may also be used. In specific embodiments, the oil additionally comprises safflower oil, sesame oil, corn oil, olive oil and/or soybean oil. In more specific embodiments, the oil additionally comprises safflower oil, and/or soybean oil.

In specific embodiments where the oil additionally comprises soy bean oil, the soybean oil may have a palmitic acid content (wt./wt) of between 9 and 13%, a stearic acid content of between 2.5% and 5%, an oleic acid content of between 17% and 30%, a linoleic acid content of between 48% and 58%, and a linolenic acid content of between 5% and 11%.

Further, in a specific embodiment, the oil-in-water emulsion compositions may comprise structured triglycerides. A "structured triglyceride" as used herein is a triglyceride comprising triglycerides or mixtures of triglycerides having at least one fatty acid group with a carbon chain length of from 6 to 12 carbon atoms and at least one fatty acid group with a carbon chain length of more than 12 carbon units.

It has been found that a high amount of omega-3-fatty acid residues improves the effect of the hormones in the treatment of the patients. Therefore, according to a specific embodiment of the invention the oil-in-water emulsion is essentially free from plant oil and/or other oil than fish oil and MCT. Essentially free within the meaning of the present invention means that the amount is less than 10 wt.-%, preferably less than 5 wt.-%, more preferably less than 2 wt.-%, especially less than 1 wt.-%, e.g. less than 0.1 wt.-%, based on the total weight of the emulsion.

In a specific embodiment, the emulsion contains no more than 0.9% wt/wt, including no more than 0.8% wt/wt, or no more than 0.5% wt/wt, of a polarity modifier selected from the group consisting of monoglycerides, diglycerides, acetylated monoglycerides, acetylated diglycerides, and/or mixtures thereof. In another specific embodiment, the emulsion contains no more than 0.9% wt./wt, including no more than 0.8% wt./wt, such as no more than 0.5% wt/wt monoglyceride.

Expressed differently, in specific embodiments the emulsion contains not more than 30%, including not more than 20%, not more than 10%, or not more than 5% by weight of phospholipid, of a polarity modifier selected from the group consisting of monoglycerides, diglycerides, acetylated monoglycerides, acetylated diglycerides and/or mixtures thereof. The use of a polarity modifier in a significant concentration relative to the phospholipid content of the emulsions may have an adverse effect on the stabilizing properties of the phospholipid.

In specific embodiments, the oil-in-water emulsion comprise 100 g/l to 300 g/l, preferably 120 g/l to 280 g/l and especially 150 g/l to 250 g/l oil, e.g. 200 g/l. In certain embodiments, a substantial proportion of the progestogen and/or estrogen is comprised within the oil droplets of the oil-in-water emulsion. In certain embodiments, in excess of 80% of the progestogen and/or estrogen is dissolved and remains within the oil droplets. In certain embodiments greater than 85%, 90%, 92%, 94%, 95%, 96%, 97%, 98%, 99% or 99.5% of the progestogen and/or estrogen is dissolved in the oil phase (determined at 20° C.).

The oil-in-water emulsion of the present invention preferably comprises an emulsifier, which is especially present in an amount of up to 50 g/l or up to 20 g/l, preferably from 2 to 15 g/l.

The oil-in-water emulsion of the present invention may further comprise one or more emulsifiers/surfactants, including phospholipid. In some embodiments, the emulsifier is of natural origin. Naturally occurring emulsifiers include soy lecithin, egg lecithin, sunflower oil lecithin, sphingosine, gangliosides, phytosphingosine, and combinations thereof. Hydrogenated lecithin, i.e. the product of controlled hydrogenation of lecithin, may also be used in the present invention.

In specific embodiments, the present composition comprises phospholipid as a surfactant. Exemplary phospholipids useful in the present invention include, but are not limited to phosphatidyl choline, phosphatidylethanolamine, phosphatidylglycerol, phosphatidic acid, and mixtures thereof. These typically have 4 to 22 carbon atoms, such as from 10 to 18 carbon atoms, and varying degrees of saturation. The phospholipid component of the compositions can be either a single phospholipid or a mixture of several phospholipids. The phospholipids employed may be natural or synthetic, but should be acceptable for parenteral, especially intravenous, administration.

A non-exhaustive list of suitable phospholipids is listed below:

Phosphatidic acids, including 1,2-Dimyristoyl-sn-glycero-3-phosphatidic acid, sodium salt (DMPA,Na), 1,2-Dipalmitoyl-sn-glycero-3-phosphatidic acid, sodium salt (DPPA,Na), 1,2-Distearoyl-sn-glycero-3-phosphatidic acid, sodium salt (DSPA,Na); phosphocholines, including 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC); phosphoethanolamines, including 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE); phosphoglycerols, including 1,2-Dilauroyl-sn-glycero-3-phosphoglycerol, sodium salt (DLPG, Na), 1,2-Dimyristoyl-sn-glycero-3-phosphoglycerol, sodium salt (DMPG, Na), 1,2-Dimyristoyl-sn-glycero-3-phospho-sn-1-glycerol, ammonium salt (DMP-sn-1-G,NH$_4$), 1,2-Dipalmitoyl-sn-glycero-3-phosphoglycerol, sodium salt (DPPG,Na), 1,2-Distearoyl-sn-glycero-3-phosphoglycerol, sodium salt (DSPG,Na), 1,2-Distearoyl-sn-glycero-3-phospho-sn-1-glycerol, sodium salt (DSP-sn-1G,Na); phosphoserines, including 1,2-Dipalmitoyl-sn-glycero-3-phospho-L-serine, sodium salt (DPPS,Na); mixed chain phospholipids, including 1-Palmitoyl-2-oleoyl-sn-glycero-3-phosphocholine (POPC), 1-Palmitoyl-2-oleoyl-sn-glycero-3-phosphoglycerol, sodium salt (POPG,Na), 1-Palmitoyl-2-oleoyl-sn-glycero-3-phosphoglycerol, ammonium salt (POPG,NH4); lysophospholipids, including 1-Palmitoyl-2-lyso-sn-glycero-3-phosphocholine (P-lyso-PC), 1-Stearoyl-2-lyso-sn-glycero-3-phosphocholine (S-lyso-PC); pegylated phospholipids, including N—(Carbonyl-methoxypolyethyleneglycol 2000)-MPEG-2000-DPPE, sodium salt, N—(Carbonyl-methoxypolyethyleneglycol 5000)-MPEG-5000-DSPE, sodium salt, N—(Carbonyl-methoxypolyethyleneglycol 5000)-MPEG-5000-DPPE, sodium salt, N—(Carbonyl-methoxypolyethyleneglycol 750)-MPEG-750-DSPE, sodium salt, N—(Carbonyl-methoxypolyethyleneglycol 2000)-MPEG-2000-DSPE, sodium salt.

In one embodiment the amount of phospholipid in the compositions according to the present invention, by weight based on the total volume of the composition, is within a range of 0.5 to 25 g/l. In certain embodiments, phospholipid may be present within a range of 0.7 to 20 g/l, including 0.8 to 18 g/l, such as 1 to 15 g/l.

In other specific embodiments, the source of the phospholipid emulsifier is lecithin, such as egg lecithin. According to the United States Pharmacopoeia (USP), lecithin is a non-proprietary name describing a complex mixture of acetone-insoluble phospholipids, which consist chiefly of phosphatidylcholine, phosphatidylethanolamine, phosphatidylserine and phosphatidylinositol, combined with various amounts of other substances such as triglycerides, fatty acids, and carbohydrates.

Soy lecithin and egg lecithin (including hydrogenated versions of these compounds) have a long history of safety in biological systems, possess combined emulsification and solubilisation properties, and tend to be metabolized in vivo into innocuous substances more rapidly than most synthetic surfactants. Commercially available soya phospholipids/lecithin are the Centrophase and Centrolex products (Central Soya), Phospholipon (Phospholipid GmbH, Germany), Lipoid (Lipoid GmbH, Germany), EPIKURON (Degussa), and PL90 (Fresenius Kabi, Sweden). In specific embodiments, the source of phospholipid is egg lecithin.

In certain embodiments the total amount of emulsifier, including phospholipid, in the compositions be within a range of 0.5 g/l to 48 g/l, specifically 0.8 g/l to 42 g/l, by weight based on the total volume of the composition. In certain embodiments, such as wherein the emulsifier is egg lecithin, the amount of emulsifier is within a range of 1 g/l to 39 g/l, such as 3 g/l to 29 g/l, including 3.5 g/l to 27 g/l, including 4 g/l to 26 g/l, especially 10 to 20 g/l such as 11 to 15 g/l.

Preferably, the emulsion comprises phospholipids comprising omega-3-fatty acid moieties, preferably phospholipids obtained from krill (Euphausiacea).

In one embodiment, the emulsifier is egg lecithin comprising 60-80% wt/wt, such as 67% wt/wt phospatidyl choline; 10-20% wt/wt, such as 15% wt./wt, phospatidlylethanolamine; <=3% wt/wt, such as 2% wt./wt, sphingomyelin; and <=3% wt/wt, such as 1% wt/wt, lysophosphatidylcholine.

"Egg lecithin PL90" (Fresenius Kabi AB) is one example of an egg lecithin having such a phospholipid content.

It has been found that omega-3-fatty acid residues improve the effect of the hormones during the therapy and prophylaxis. Therefore, according to a particular preferred embodiment the oil-in-water emulsion comprises phospholipids having omega-3-fatty acid moieties, preferably phospholipids obtained from krill (Euphausiacea).

Phospholipids comprising omega-3 fatty acid residues can be obtained from Krill. For example, the krill oil can contain omega-3 fatty acid-containing phospholipids in an amount of about 20 to about 60%, for example, from about 30 to about 50%, based on the weight of the krill oil. In an exemplary embodiment, the krill oil can contain omega-3 fatty acid-containing triglycerides in an amount of less than about 30%, for example, less than about 5%, based on the weight of the krill oil. In an exemplary embodiment, the krill oil can be substantially free of omega-3 fatty acid-containing triglycerides. For example, both phospholipids (PLs) and triglycerides (TGs) possess a 3-carbon backbone (triacylglycerol) where certain functional groups attach to each of the carbons, with positions-1, -2, and -3 noted as sn1, sn2 and sn3, respectively. The sn1 and sn2 positions in both PLs and TGs can contain long-chain fatty acids, such as 18-carbon compounds (e.g., linoleic, alpha-linolenic, oleic and stearic acids) and/or very-long chain fatty acids containing 20 or more carbons (e.g., arachidonic, eicospentaenoic, docsapentaenoic and docosahexaenoic acids). In TGs, the sn3 position is also occupied by the above long-chain fatty acids, and as such these compounds are known as "neutral fat", whereas in PLs the sn3 position is occupied by phosphoric acid bound to an alcohol such as choline, ethanolamine, serine, inositol, etc., that significantly alters the molecule, conferring to it both hydrophilic and hydrophobic properties, known as an amphiphilic compound. As part of the structural make-up of biological membranes, and possessing amphiphilic properties, PLs serve a vital role in many metabolic processes.

In an exemplary embodiment, a pre-determined amount of the omega-3 fatty acid-containing phospholipids contain omega-3 fatty acids attached to the first and second positions of the phospholipid, but not the third position of the phospholipid. That is, a predetermined amount of the omega-3 fatty acid-containing phospholipids can contain an omega-3 fatty acid in the second position (i.e., the middle position) of the phospholipid. For example, the omega-3 fatty acid-containing phospholipids containing omega-3 fatty acids attached to the first and second positions of the phospholipid, but not the third position of the phospholipid, can be present in an amount of about 70% to about 80%, for example, from about 80% to about 95%, based on the total weight of the omega-3 fatty acid-containing phospholipids.

According to another exemplary aspect, a method of parenterally administering the oil-in-water emulsion is provided, the method comprising parenterally administering to a person a composition containing phospholipids obtained from marine crustacean in a parenteral oil-in-water emulsion that contains protective concentrations of the naturally-occurring anti-oxidant, astaxanthin, against chemical breakdown or oxidation of the unsaturated omega-3 fatty acids present. Oxidation of the polyunsaturated omega-3 fatty acid leads to the formation of reactive oxygen species that may be harmful upon intravenous administration. Thus, a specific omega-3 fatty acid rich oil-in-water emulsion needs protection against chemical breakdown. Astaxanthin, found in krill oil, may provide unique protection against the oxidation of the omega-3 fatty acids similar to the presence of alpha-tocopherol in soybean oil that protects against oxidation of the omega-6 fatty acids. As such, just as marine-based phospholipids found in krill oil contain a high concentration of n3-FAs which may uniquely enhance the physical stability of the emulsion, so too may the presence of astaxanthin in krill oil uniquely enhance the chemical stability of the oil-in-water emulsion. Like the exemplary aspects of krill oil as a primary surfactant, or co-surfactant with egg phospholipids, it might be that astaxanthin can be the primary antioxidant, or co-antioxidant with alpha-tocopherol.

A further alternative embodiment of the present invention is a hormone containing oil-in water emulsion for parenteral administration comprising a) progestogen and/or estrogen as defined above and b) a phospholipid obtained from marine crustacean as defined above.

In one embodiment, the emulsion comprises no more than 1.5% wt/wt, no more than 1.2% wt/wt, or no more than 0.8% wt/wt, including no more than 0.4% wt/wt, of polyethylene glycol 15-hydroxystearate. In another embodiment, the compositions comprise no more than 1.5% wt/wt, no more than 1.2% wt/wt, or no more than 0.8% wt/wt, including no more than 0.4% wt/wt, polyethylene glycol ester and/or polyethylene-propylene glycol.

In accordance with some embodiments, the present invention provides pharmaceutical compositions comprising progestogen and/or estrogen, wherein said compositions are in the form of an emulsion comprising an aqueous phase, an oil phase, and a surfactant.

Aqueous Medium

As noted above, the oil-in-water emulsion of the present invention further comprise an aqueous medium. "Aqueous medium" or "aqueous phase" refers to a water-containing liquid. In some embodiments, the aqueous medium is water and/or an aqueous buffer solution.

The oil-in water emulsion of the invention may comprise 70 to 98 wt.-%, preferably 70 to 90 wt.-%.

In some embodiments, the emulsion may comprise 0 to 4 mM of a physiologically compatible buffering agent.

In some embodiments, the oil-in water emulsions according to the present invention optionally comprise a co-surfactant. Co-surfactants suitable for use in the emulsions of the present invention are those that prevent flocculation and/or coalescence of the lipid emulsion. Exemplary co-surfactants include, but are not limited to cholesterol, oleic acid, oleate, Tween80 (PEG-sorbitan monooleate), HCO-60, Solutol H15 (polyoxyethylene-66β-hydroxystearate), PEG-400 (polyethylene glycol), Pluronic F68 (BASF), Cremophor EL (polyoxyethylene-35-ricinoleate), or the salt of a bile acid, such as deoxycholic acid. In other embodiments the co-surfactant is selected from the group consisting of C12-C22 fatty acids, salts thereof, and/or mixtures thereof, such as from C16-C20 fatty acids, salts thereof, and/or mixtures thereof, or from C18 fatty acids, salts thereof, and/or mixtures thereof. In specific embodiments, the fatty acid is mono-unsaturated.

In some embodiments the co-surfactant may be present in compositions in an amount (wt/vol) greater than or equal to 0.005%, greater than or equal to 0.01%, or greater than or equal to 0.02%. In accordance with any of these embodiments the co-surfactant may be present in an amount (wt/vol) less than or equal to 4%, less than or equal to 1%, or less than or equal to 0.04%.

In specific embodiments, the co-surfactant is selected from the group consisting of long-chain fatty acids, such as palmitic acid, oleic acid or stearic acid, or the alkali salts thereof. Oleate and/or oleic acid, particularly sodium oleate, are particularly suitable co-surfactants.

In certain embodiments where the co-surfactant is oleate and/or oleic acid, the co-surfactant may be present in an amount (wt/vol) equal to or greater than 0.005%, equal to or greater than 0.01%, or equal to or greater than 0.02%. In accordance with any of these embodiments, the co-surfactant may be present in an amount (wt/vol) less than or equal to 0.5%, less than or equal to 0.2%, less than or equal to 0.1%, or less than or equal to 0.05%. In specific embodiments, the co-surfactant is sodium oleate and is present in an amount of 0.03% wt/vol (0.3 g/l). The emulsions described herein may be suitable for parenteral infusion, such as intravenous injection or intravenous infusion, over prolonged periods. A typical duration of treatment may be, e.g. 3-7 days. In specific embodiments, the concentration of certain co-surfactants therefore is kept to a minimum to prevent side effects such as irritation, cytochrome P450 inhibition, etc. In specific embodiments, Pluronic F68 (poly(ethyleneglycol)-13-poly(propylene glycol co-propylene glycol) is present in an amount less than 0.7% (wt/wt), or less than 0.5% (wt/wt). In other specific embodiments, Solutol-HS (Macrogol-15-hydroxystearate) is present in an amount less than 1.2% (wt/wt), or less than 1% (wt/wt).

Osmotic Agent

The oil-in water emulsion according to the invention may comprise an osmotic agent and/or a tonicity modulator. Such compositions may have an osmolality in the range of 200-1000 mOsm/kg.

In accordance with specific embodiments of the invention the emulsions may be isotonic and iso-osmotic. The compositions may have an osmolality of 220-600 mOsm/kg, or 230-360 mOsm/kg.

Suitable osmotic and/or tonicity modulating agents include potassium or sodium chloride, trihalose, sucrose, sorbitol, glycerol, glucose, xylitol, mannitol, polyethylene glycol, propylene glycol, albumin, amino acid and mixtures thereof. In certain embodiments, an osmolality of 270 to 330 mOsm/kg, such as 280 to 300 mOsm/kg, is achieved with an agent that also increases osmotic pressure, such as glycerol, dextrose, lactose, sorbitol or sucrose.

In one embodiment, the osmotic agent is a physiologically acceptable polyol, such as glycerol, sorbitol or xylitol. In a specific embodiment, the osmotic agent is glycerol.

The osmotic agent and/or tonicity regulating agent is generally used in an amount that does not have adverse biological effects, but is sufficient to provide isosmotic and/or isotonic compositions. When glycerol is the osmotic agent, glycerol may be present in the range of 2 to 5% (wt/vol), such as 2.1% to 2.9% (wt/vol), including 2.3% to 2.7%. In specific embodiments, the emulsions of the present invention comprise 2.5% glycerol (25 g/l).

pH Regulating Agent

In some embodiments, the emulsions according to the present invention have a pH within the range of pH 6.0 to pH 9.0, such as pH 6.5 to pH 8.5, including pH 7.0 to 8.0. The pH of the compositions may be adjusted by methods known in the art, e.g., through the use of an appropriate base that neutralizes the negative charge on the fatty acids, through the use of an appropriate buffer, or a combination thereof. A variety of bases and buffers are suitable for use with the emulsions of the present invention. One skilled in the art will appreciate that the addition of buffer to the emulsion will affect not only the final pH, but also the ionic strength of the emulsion. High ionic strength buffers may negatively impact the zeta potential of the emulsion and are, therefore, not desirable. In a specific embodiments, the pH is adjusted to the desired value by addition of 1N sodium hydroxide.

Optional Additives

The emulsion according to the present invention optionally comprise one or more pharmaceutically acceptable additives, such as binding, chelating, complexing agents, preservatives (including antimicrobials and antioxidants), viscosity modifying agents and other biocompatible materials or therapeutic agents.

Ratios of Composition Components

While exemplary amounts of different components that may be included in the compositions of the invention are set forth above, other aspects of the invention relate to ratios of specific components, as discussed below.

Emulsifier (Phospholipid): Oil

It was found that excess amounts of phospholipid in oil-in-water emulsions can lead to an increase in phospholipid degradation products following autoclaving and/or storage, causing a drop in pH, which in turn negatively impacts upon emulsion stability.

In a preferred embodiment, such as wherein the emulsifier is phospholipid, the emulsions comprise the emulsifier in an amount (expressed as % wt./wt of the total oil component) within the range of 6.8 to 43%, such as 8.4 to 42.5%, including 12-26%, such as 14-25%, including 15 to 22%. In a specific embodiment, the emulsifier is phospholipid and is present in an amount of 16-18% (wt/wt) of the oil.

In further preferred embodiments, the oil-in water emulsions comprise phospholipid in an amount expressed as % wt/wt of the oil, greater than or equal to 6.8%, greater than or equal to 8.4%, greater than or equal to 12%, greater than or equal to 14%, or greater than or equal to 15%. In some embodiments, the compositions comprise phospholipid in an amount expressed as % wt/wt of the oil, of less than or equal to 43%, less than or equal to 42.5%, less than or equal to 26%, less than or equal to 25%, or less than or equal to 22%.

In another preferred embodiment of the present invention, such as wherein the source of phospholipid is lecithin, the compositions comprise lecithin in an amount within the range of 3 to 20% of the oil (wt/wt), such as 4 to 18% of the oil (wt/wt), including 6-16% of the oil (wt/wt), such as 8-14% of the oil (wt/wt). In a specific embodiment, the emulsifier is egg lecithin and is present in an amount of 19-21% (wt/wt) of the oil.

In some embodiments, the emulsions of the present invention comprise lecithin, such as egg lecithin, in an amount expressed as % wt/wt of the oil, of greater than or equal to 8%, greater than or equal to 10%, greater than or equal to 13%, greater than or equal to 15%, or greater than or equal to 18%. In some embodiments, the compositions comprise lecithin, such as egg lecithin, in an amount expressed as % wt/wt of the oil, of less than or equal to 50%, less than or equal to 48%, less than or equal to 40%, less than or equal to 33%, or less than or equal to 31%.

Co-Surfactant: Oil

As noted above, in certain embodiments of the present invention, the compositions comprise a co-surfactant, such as oleate or oleic acid. In specific embodiments, the co-surfactant may be present in an amount expressed as % wt/wt of the oil component, within the range of 0.08 to 2%, such as 0.1 to 0.9%, including 0.3 to 0.7%. In another embodiment, the co-surfactant is present in an amount greater than 0.02% wt/wt of said oil. In a specific embodiment, the co-surfactant is oleate or oleic acid, and is present in an amount of 0.5% of the oil (wt/wt).

In some embodiments, the co-surfactant is present in an amount expressed as % wt/wt of the oil, of greater than 0.02, greater than or equal to 0.08%, greater than or equal to 0.1%, or greater than or equal to 0.3%. In other embodiments, the concentration of co-surfactant, in an amount expressed as % wt/wt of the oil, is less than or equal to 2%, less than or equal to 0.9%, or less than or equal to 0.7%.

Co-Surfactant: Emulsifier (Phospholipid)

In a preferred embodiment of the present invention, the compositions comprise phospholipid as an emulsifier, and a co-surfactant, such as oleate. In specific aspects of these embodiments the co-surfactant and the emulsifier may be present in a co-surfactant to phospholipid ratio (wt/wt) within the range of 1:85 to 1:12, such as 1:82 to 1:17, including 1:68 to 1:20, such as 1:51 to 1:26, including 2:85 to 1:34.

In preferred embodiments, the co-surfactant and the phospholipid are present in a co-surfactant to phospholipid ratio (wt/wt) greater than or equal to 1:85, greater than or equal to 1:82, greater than or equal to 1:68, greater than or equal to 1:51, or greater than or equal to 2:85. In some embodiments, the co-surfactant and the phospholipid are present in a co-surfactant to phospholipid ratio (wt/wt) less than or equal to 1:12, less than or equal to 1:17, less than or equal to 1:20, less than or equal to 1:26, or less than or equal to 1:34.

In another preferred embodiment of the present invention, the compositions comprise egg lecithin as an emulsifier, and a co-surfactant, such as oleate. In specific aspects of these embodiments, the co-surfactant and the emulsifier may be present in a co-surfactant to lecithin ratio (wt/wt) within the range of 1:100 to 1:15, such as 1:80 to 1:20, including 1:70 to 3:70, such as 1:60 to 1:30, including 1:50 to 1:40.

In specific embodiments, the co-surfactant and the lecithin are present in a co-surfactant to lecithin ratio (wt/wt) greater than or equal to 1:100, greater than or equal to 1:80, greater than or equal to 1:70, greater than or equal to 1:60, or greater than or equal to 1:50. In some embodiments, the co-surfactant and the lecithin are present in a ratio (wt/wt) less than or equal to 1:15, less than or equal to 1:20, less than or equal to 3:70, less than or equal to 1:30, or less than or equal to 1:40.

In a specific embodiment wherein the co-surfactant is oleate and the emulsifier is egg lecithin, the co-surfactant to emulsifier ratio (wt/wt) is within the range of 1:45 to 1:20, such as 1:40 to 1:25.

Packaging

The oil-in-water emulsion of the present invention may be provided as ready-to-use compositions. "Ready-to-use" as used herein means that no further formulation, such as diluting or mixing together of multiple components, is required.

The oil-in-water emulsion of the present invention may be provided in sealed packaging. The packaging should be compatible for use with lipid formulations and progestogens and/or estrogen. Examples of materials less suitable for packaging of oily formulations include PVC and DEHP. Suitable packaging which is compatible with oily formulations includes but is not limited to polypropylene-based bags and glass bottles. Conventional glass is a suitable packaging material for compositions of the present invention. In specific embodiments, the emulsion is packaged in a sealed container. The container may be overwrapped to provide protection from the physical environment. In one embodiment, the composition is packaged in a sealed container having a volume of 250 ml. In one embodiment, the oil-in-water emulsion is packaged in sealed container under a headspace of inert gas.

In some embodiments the compositions are packaged in inert containers. In some embodiments, the inert containers are light occluded. In other embodiments, the container comprises a double-layered wall, and, in more specific embodiments, the area between the two layers is filled with an inert gas in order to prevent oxidation. For prolonged storage, the packaging material advantageously prevents the diffusion of oxygen from the ambient air towards the compositions of the invention, to prevent the formation of oxygen degradants within the compositions.

In some embodiments, the composition is packaged in a unit dose. A unit dose may provide sufficient composition for administration of a progestogen and/or estrogen bolus dose to a subject, or for administration of the composition over a predetermined period of time such as the first hour, first 2 hours, first 4 hours, etc., of treatment. The unit dose enables rapid and convenient administration of the composition in emergency situations, for example by paramedics in the ambulance, or by first aiders/medics at the location an injury/event occurs. Non-limiting examples of unit dose forms are injections, pre-filled syringes, glass vials, and/or sealed bags.

In some embodiments, the composition is packaged within a device similar to an insulin-pump device, which is used to administer a continuous infusion therapy, or in a cartridge designed for use with such a device. Exemplary insulin pumps are those marketed by MiniMed and Disetronic. Such pumps may comprise for example, a cannula, a pump reservoir or cartridge in which the composition is stored, a pump which may be battery operated, and means of allowing the user to control the exact amount of active being delivered, such as for example, a computer chip.

Specific Example

In one specific embodiment, the emulsion of the present invention comprises
  a) progesterone in an amount ranging from 1.0 to 2.0 g/l;
  b) 100 to 300 g/l, based on the oil-in-water emulsion, of an oil component comprising
    i) at least 50 wt.-% of fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty acids and preferably the total amount of omega-3-fatty acids is at least 50% by weight of said fatty acids; and
    ii) 10 to 50 wt.-% of MCT, based on the total weight of the oil component;
  c) 4 to 20 g/l of a phospholipid, preferably 8 to 20 g/l of a phospholipid and
  d) 10 to 50 g/l of glycerol.

In one specific embodiment, the emulsion of the present invention comprises
  a) estradiol in an amount ranging from 0.05 to 1.0 g/l and progesterone in an amount ranging from 1.0 to 2.0 g/l;
  b) 100 to 300 g/l, based on the oil-in-water emulsion, of an oil component comprising
    i) at least 50 wt.-% of fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty acids and preferably the total amount of omega-3-fatty acids is at least 50% by weight of said fatty acids; and ii) 10 to 50 wt.-% of MCT, based on the total weight of the oil component;
c) 4 to 20 g/l of a phospholipid, preferably 8 to 20 g/l of a phospholipid and
d) 10 to 50 g/l of glycerol.

In one specific embodiment, the emulsion of the present invention comprises
a) estradiol in an amount ranging from 0.05 to 1.0 g/l;
b) 100 to 300 g/l, based on the oil-in-water emulsion, of an oil component comprising
   i) at least 50 wt.-% of fish oil triglycerides, wherein the fish oil triglyceride consists of glycerol which is esterified with fatty acids wherein said fatty acids comprise eicosapentaenoic acid (EPA) and docosahexaenoic acid (DHA) in an amount of at least 45% by weight of said fatty acids and preferably the total amount of omega-3-fatty acids is at least 50% by weight of said fatty acids; and
   ii) 10 to 50 wt.-% of MCT, based on the total weight of the oil component;
c) 4 to 20 g/l of a phospholipid, preferably 8 to 20 g/l of a phospholipid and
d) 10 to 50 g/l of glycerol.

Properties of the Emulsion

Compositions according to the present invention typically are milky white in appearance, and present as visually homogenous emulsions.

Emulsion Droplet Particle Size Distribution

PFAT5 Value

The United States Pharmacopeia (USP) sets the limit for globule size distribution in lipid injectable emulsions (USP 729-Pharm. Forum. 2005; 3:1448-1453). The limit for fat globules of diameter>5 μm in injectable emulsions, expressed as volume-weighted percentage fat>5 μm is not exceeding 0.05%, or PFAT5 not exceeding 0.05% (USP 729-Pharm. Forum. 2005; 3:1448-1453). Compositions having a PFAT5, value exceeding 0.05% are considered to be unsafe for intraveneous administration. The PFAT5 value of an emulsion may be influenced by several factors including the total oil content of the emulsion, the type and amount of phospholipid, the choice of co-surfactant, the co-surfactant-to-oil ratio, and the stability of the emulsion droplets to coalescence and/or flocculation.

In specific embodiments, the compositions according to the present invention have a PFAT5 value of less than or equal to 0.05%, such as less than or equal to 0.04%, including less than or equal to 0.02%, such as less than or equal to 0.01%.

In one embodiment, 100% of the emulsion droplets of a composition of the present invention are less than or equal to 5 μm in diameter, and at least 98% of droplets, including 99% of droplets, are less than or equal to 1.5 μm diameter. The particle size distribution of droplets greater than 1 μm in diameter is determined by Coulter counter (Coulter Multisizer III).

PCS

In one embodiment, the droplets less than or equal to 1 μm in diameter have a maximum PCS z-average of 350 nm, and/or a PCS polydispersion value of no more than 0.25. In a specific embodiment, the droplets less than or equal to 1 μm in diameter have a maximum z-average of 250 nm, and/or a polydispersion value of no more than 0.20. In an even more specific embodiment, the droplets less than or equal to 1 μm in size have a maximum z-average of 220 nm, and/or a polydispersion value of no more than 0.15.

Median Droplet Size

The emulsion droplet size is the key parameter determining the kinetics of emulsion destabilisation, since droplet size directly influences the rate of phenomena such as, coalescence, creaming, flocculation, ostwald ripening and ultimately phase separation. Emulsion droplet size is therefore indicative of emulsion stability. Multiple parameters influence emulsion droplet size, including for example the oil-type, surfactant and co-surfactant type, presence of active ingredients, the amount of oil, oil-to-surfactant and oil-to-co-surfactant ratios. In a specific embodiment, the compositions according to the present invention maintain a volume based median diameter, or D[4,3], of <=300 nm, such as <=230 nm, including about <=200 nm, such as <=185 nm, including about <=180 nm, following autoclaving at 121° C. for 15 mins, and/or following storage at 60° C. for at least 3 weeks, including 4 weeks.

Mean Droplet Size

In one embodiment, the emulsion droplet particles of compositions according to the present invention have a volume based mean diameter, or d(0,5) of <=320 nm, such as <=250 nm, including <=200 nm, such as <=185 nm, including <=180 nm. Preferably, the droplet particles are ranging from 240 to 320 nm.

In a specific embodiment, the compositions according to the present invention maintain a volume based mean diameter, or d(0,5) of <=300 nm, such as <=250 nm, including <=200 nm, such as <=185 nm, including <=180 nm, following autoclaving at 121° C. for 15 mins, and/or following storage at 60° C. for at least 3 weeks, including 4 weeks.

Zeta-Potential

The zeta potential is related to the stability of the emulsion. Emulsions with a high zeta potential are electrically stabilized while those with low zeta potentials tend to coagulate or flocculate. The zeta potential of emulsions is influenced for example by the choice and amount of surfactant and co-surfactant, the pH of the emulsions, as well as ionic strength of the aqueous solution.

In one embodiment, compositions of the present invention have a zeta potential within the range of, −30 mV to −70 mV, such as −40 mV to −65 mV, including −51 mV to −60 mV. In addition, the zeta potential of the emulsion compositions of the present invention may be −30 mV, −35 mV, −40 mV, −45 mV, −50 mV, −55 mV, −60 mV, −65 mV or −70 mV or higher.

Particulate Matter

In certain embodiments the emulsions of the present invention are free of crystalline solid at ambient temperature (e.g., at one or more temperatures selected from 4° C., from 2° C. to 8° C. or from 20° C. to 25° C.). In specific embodiments, the emulsion compositions of the present invention meet the standards for particulate size and count in injection liquids (USP 788, Method 2-Microscopic Particle count test). For example, the compositions may contain 0-12 particles per ml equal to or greater than 10 μm and 0-2 particles per ml equal to or greater than 25 μm.

Stability of the Emulsions

Sterility

In specific embodiments, the emulsions according to the present invention are sterile. As used herein "sterile" refers to compositions meeting the requirements of USP Chapter <71>. In specific embodiments the compositions meet the requirements of USP Chapter <85> "Bacterial endotoxin test", and optionally additionally meet the requirements of the USP Chapter <151> "pyrogen test"

In specific embodiments, the emulsions of the present invention achieve improved progesterone and/or estrogen solubility, whilst maintaining, or improving, the chemical stability and/or physical stability of the emulsions. In specific embodiments, the compositions may be heat-sterilized by autoclaving at 121° C. for 15 minutes without compromising the physical or chemical integrity of the emulsions. Sterilization by autoclaving is beneficial not only in terms of microbiological safety, but also is financially more cost-effective, as compared for example to filter sterilizing.

Furthermore, in specific embodiments, the emulsions exhibit safety advantages over the prior art, such as for example, (a) the compositions meet the standards for particle size and count in injection liquids (USP 788, Method 2) and/or comprise a lesser level of progestogen and/or estrogen crystals, (b) the compositions have a low PFAT5 value (as discussed in more detail above), (c) the compositions contain lower levels of chemical impurities, (d) the compositions may be autoclaved using the gold standard method for microbiological safety, and/or (e) the compositions do not comprise alcohol or potentially toxic organic solvents.

As a result of one or more of the above-described advantages of the compositions described herein, the emulsions provide an improved availability of the progestogen contained therein (e.g., good pharmacokinetics and bioavailability, such as may be reflected in serum hormone levels and/or plasma concentration), and administration of the emulsions provides improved consistency in patient dosing, relative to compositions of the prior art.

Finally the emulsion compositions according to the present invention in addition to being convenient and safe to use, are advantageously provided in a sterile, ready-to-use form, have a shelf life of 1 or 2 years at room temperature.

Manufacturing Process

A further embodiment of the present invention is a process for the preparation of the oil-in water emulsion of the invention.

The process comprises the steps of:
a) dissolving progestogen and/or estrogen in an oil phase comprising fish oil triglycerides, wherein the fish oil triglycerides consists of glycerol which is esterified with fatty acids wherein said fatty acids comprise eicosapentaenoic acid (EPA) and docosahexaenoic acid (DHA) in an amount of at least 45% by weight of said fatty acids and preferably the total amount of omega-3 fatty acids is at least 60% by weight of said fatty acids;
b) emulsifying the oil phase in the aqueous phase, preferably in the presence of an emulsifier.

In another aspect, the present invention relates to a method of manufacturing the oil-in-water emulsion compositions as defined herein before, said method comprising the steps of:
a) combining water, and phospholipid, and optionally an osmotic agent to produce an aqueous composition;
b) combining progestogen and/or estrogen and oil to produce an oily composition; and
c) combining the aqueous composition and the oily composition followed by homogenization to form a homogenous oil-in-water emulsion.

According to a specific embodiment, the aqueous composition is homogenized so as to produce a homogeneous suspension, before said aqueous composition is combined with the oily composition. In another advantageous embodiment, the progestogen and/or estrogen is added to oil having a temperature of at least 40° C. to facilitate dilution of the progestogen and/or estrogen. In other specific embodiments, the oily composition is filtered before it is combined with the aqueous composition.

In some very specific embodiments, the methods of manufacture comprise the following steps:
A) dissolving an optional osmotic agent in an aqueous medium and stirring;
B) adding emulsifier, such as egg lecithin, and stirring;
C) optionally adding a co-surfactant and optionally a pH regulating agent and mixing;
D) dissolving progestogen and/or estrogen in oil to form an oil phase;
E) filtering the oil phase, followed by addition of the filtered oil phase to the aqueous phase, and mixing;
F) homogenization to form a homogenous emulsion;
G) optional addition of water;
H) optional addition of sufficient 1N NaOH to adjust the pH to pH 8.0-8.8;
I) optional addition of sufficient aqueous medium to achieve the final volume.

In a specific embodiment, the homogenization is performed at greater than or equal to 350 bar, or greater than or equal to 370 bar.

In specific embodiments, the methods of manufacturing of the emulsions involve the steps of dissolving the egg lecithin in aqueous medium (rather than in oil), adding the oil phase to the aqueous phase (rather than vice versa), and homogenization at greater than or equal to 350 bar. These steps are believed to result in emulsions with advantageous properties in terms of particle size and emulsion stability.

In another specific embodiments, the emulsion is packaged in sealed containers, and sterilized, such as by heating to at least 121° C. (e.g. 121° C. to 123° C.) for a minimum of 15 mins holding time. The autoclave program may be a rotary cycle.

In other very specific embodiments, the methods of manufacture comprise the following steps:
A) dissolving an osmotic agent in an aqueous medium and stirring;
B) adding phospholipid, specifically egg lecithin and stirring;
C) optionally adding a co-surfactant and a pH regulating agent and mixing;
D) dissolving progesterone and/or estrogen in the fish oil triglycerides to form an oil phase;
E) filtering the oil phase, followed by addition of the filtered oil phase to the aqueous phase, and mixing;
F) homogenization to form a homogenous emulsion;
G) optional addition of water;
H) optional addition of sufficient 1N NaOH to adjust the pH to pH 8.0-8.8;
I) optional addition of sufficient aqueous medium to achieve the final volume.

The following provides a detailed example of a method of manufacture. The skilled artisan readily will understand that various modifications and variations can be made, and still fall within the scope of the invention.

Method of Treatment

A further embodiment of the present invention is a pharmaceutical composition comprising or consisting of the oil-in water emulsion of the present invention.

Preferably, the pharmaceutical composition of the present invention is for use in the treatment or prophylaxis of neurological damage after strokes and/or trauma.

According to a further preferred embodiment the pharmaceutical composition of the present invention is for use in the treatment of prophylaxis of neurological damage after concussion or for use in the treatment of prophylaxis of traumatic events.

The emulsions described herein may be administered parenterally, such as intravenously or intra-arterially, to subjects for therapeutic or prophylactic use. In specific embodiments the subject is a mammal, such as a human.

The emulsions described herein have neuro-protective and/or neuro-regenerative properties. The compositions therefore are useful in the treatment or prevention of nervous system disorders or conditions. Exemplary disorders and conditions include, but are not limited to, central nervous system (CNS) disorders or conditions, spinal chord injury, traumatic brain injury, mild head injury, including concussion characterized by a temporary loss of brain function, pediatric brain injury, degenerative disorders of the CNS such as Parkinson's disease, dementia, including Alzheimer's disease, demyelinating conditions such as multiple sclerosis and chronic, diabetic peripheral neuropathology.

Other exemplary disorders and conditions include ischemic neurological conditions, such as ischemic CNS injury, stroke, including ischemic stroke, hemorrhagic stroke and transient ischemic attacks, and neurocognitive impairments attributed to cardiopulmonary bypass during cardiac surgery, for example post-perfusion syndrome. Further examples include asphasia, sleep disorders, and anxiety disorders such as post-traumatic stress disorder.

The compositions are also useful to provide relief of symptoms associated with the above-listed disorders, such as restoring cognitive function, restoring sleep patterns, normalizing mood disorders, etc. The pharmaceutical compositions are also useful to treat post-traumatic stress disorders.

In accordance with one embodiment, the present invention provides methods of treating a mammalian subject with a traumatic CNS injury, such as a traumatic brain injury. Exemplary methods comprise treatment of a TBI in a mammalian subject by administering to the subject in need thereof a pharmaceutical composition according to the present invention, such that a therapeutically effective concentration of progestogen and/or estrogen is delivered. In a specific embodiment the mammalian subject is a human. For example, the methods of the present invention may comprise parenterally administering the progestogen- and/or estradiol-comprising pharmaceutical compositions of the present invention to a subject having a traumatic CNS injury, such as a TBI. In accordance with the method of the present invention, the pharmaceutical composition is used to promote a positive therapeutic response with respect to the traumatic central nervous system injury.

Traumatic brain injury is physical injury to brain tissue that temporarily or permanently impairs brain function. Diagnosis is suspected clinically and may be confirmed by imaging (primarily CT). Clinical manifestations vary markedly in severity and consequences. Injuries are commonly categorized as open or closed. Open injuries involve penetration of the scalp and skull. Closed injuries typically occur when the head is struck, strikes an object, or is shaken violently, causing rapid brain acceleration and deceleration.

The pharmaceutical compositions of the invention can be used to treat a TBI, including blunt traumas (e.g., closed injuries), as well as penetrating traumas. By "treatment" is intended any improvement in the subject having the traumatic CNS injury, including both improved morphological recovery (i.e., enhanced tissue viability) and/or behavioral recovery. The improvement can be characterized as an increase in either the rate and/or the extent of behavioral and anatomical recovery following the traumatic CNS injury. Accordingly, a "positive therapeutic response" includes both a complete response and a partial response. Various methods to determine if a complete or a partial therapeutic response has occurred are discussed in detail in patent applications WO2006/102644, WO2006102596, and WO2008/039898.

By "therapeutically effective amount" is meant an amount of progestogen and/or estrogen that is sufficient to elicit a therapeutic effect. Thus, in some embodiments, the amount of a progestogen and/or estrogen in an administered dose unit in accordance with the present invention is effective in the treatment or prevention of neuronal damage that follows a traumatic injury to the CNS and hence, elicits a neuroprotective effect. Neurodegeneration is the progressive loss of neurons in the central nervous system. As used herein, "neuroprotection" is the arrest and/or reverse of progression of neurodegeneration following a traumatic CNS injury. The therapeutically effective amount will depend on many factors including, for example, the specific activity of the progestogen and/or estrogen, the severity and pattern of the traumatic injury, the resulting neuronal damage, the responsiveness of the patient, the weight of the patient, along with other intra-person variability, the mode and/or method of administration, and the pharmaceutical composition used.

The pharmaceutical compositions of the present invention may be administered using any acceptable method known in the art, including intravenous (IV) injection, intramuscular (IM) injection, or subcutaneous (SC) injection. In specific embodiments of the invention, the composition is administered intravenously, such as by IV injection. When administered intravenously, the composition can be administered by infusion over a period of from 1 to 144 hours.

Progestogen and/or estrogen may be administered once or several times a day. The duration of the treatment may be once per day for a period of 1, 2, 3, 4, 5, 6, 7 days or more. The daily dose can be administered either by a single dose in the form of an individual dosage unit or several smaller dosage units or by multiple administration of subdivided dosages at certain intervals. Subsequent dosage units can be administered any time following the initial administration such that a therapeutic effect is achieved. For instance, additional dosage units can be administered to protect the subject from the secondary wave of edema that may occur over the first several days post-injury. In a specific embodiment, the first dosage unit is administered no later than from 8 hours post-injury.

In specific embodiments of the invention, the progestogen and/or estrogen is administered in a constant dosing regimen. By "constant dosing regimen" is meant that the progestogen and/or estrogen is administered in a constant total hourly infusion dose of progestogen and/or estrogen over the course of treatment.

In further embodiments of the present invention, at least one additional neuroprotective agent can be administered in combination with the progestogen and/or estrogen (either as part of the same composition or in a separate composition) to enhance neuroprotection following a traumatic CNS injury.

Having now generally described this invention, the same will be better understood by reference to certain specific examples which are included herein for purposes of illustration only, and are not intended to be limiting of the invention.

EXAMPLES

General Procedure for the Preparation of a Hormone-Containing Oil Emulsion

After mixing of glycerol and a part of the water, the emulsifier (egg lecithin) and the co-emulsifier sodium oleat are dispersed by Ultra Turrax® cell homogenizer (solution I). Parallel the oil phase, optional with tocopherol, is prepared and estradiol and progesterone are dissolved by 70° C. under nitrogen inert atmosphere (solution II). Solution II is added to solution I using an Ultra Turrax cell homogenizer followed by 4 to 5 homogenization cycles in a high-pressure homogenizer under at least 400 bar to 800 bar by 30° C. to 70° C. Then the rest of the water is added and the pH value of the resulting oil-in-water emulsion is adjusted to 7.5 to 9.0 with sodium hydroxid possible as solution.

After being filled into a container of suitable quality, the emulsion is heat-sterilized by known methods. A sterile and stable o/w emulsion with lipid droplets having an average oil droplet size of less than 0.5 μm and a storage stability of at least 18 months results.

TABLE 1

| | amount pro 1000 ml | amount pro 30 l |
|---|---|---|
| progesterone | 1.500 g | 45.00 g |
| estradiol | 0.150 g | 4.500 g |
| medium chain triglycerides | 20.0 g | 600.0 g |
| fish oil triglyceride [1] | 180.0 g | 5400.0 g |
| egg lecithin | 12.00 g | 360.0 g |
| glycerol | 25.00 g | 750.0 g |
| Sodium oleate | 0.300 g | 9.0 g |
| α-tocopherol | 0.200 g | 6.0 g |
| NaOH | max 0.06 g | max. 1.8 g |
| water for injection | ad 1000 ml | ad 30.0 l |

[1] The amount of EPA and DHA is 55.5 wt.-%, based on the total amount of fatty acids in the fish oil triglyceride. The weight ratio of EPA to DHA is 3:2.

TABLE 2

| | amount pro 1000 ml | amount pro 30 l |
|---|---|---|
| progesterone | 1.500 g | 45.00 g |
| estradiol | 0.150 g | 4.500 g |
| medium chain triglycerides | 60.0 g | 1800.0 g |
| fish oil triglyceride [1] | 140.0 g | 4200.0 g |
| egg lecithin | 12.00 g | 360.0 g |
| glycerol | 25.00 g | 750.0 g |
| Sodium oleate | 0.300 g | 9.0 g |
| α-tocopherol | 0.200 g | 6.0 g |
| NaOH | max 0.06 g | max. 1.8 g |
| water for injection | ad 1000 ml | ad 30.0 l |

[1] The amount of EPA and DHA is 55.5 wt.-%, based on the total amount of fatty acids in the fish oil triglyceride. The weight ratio of EPA to DHA is 3:2.

TABLE 3

| | amount pro 1000 ml | amount pro 30 l |
|---|---|---|
| progesterone | 1.500 g | 45.00 g |
| estradiol | 0.150 g | 4.500 g |
| medium chain triglycerides | 100.0 g | 3000.0 g |
| fish oil triglyceride [1] | 100.0 g | 3000.0 g |
| egg lecithin | 12.00 g | 360.0 g |
| glycerol | 25.00 g | 750.0 g |
| Sodium oleate | 0.300 g | 9.0 g |
| α-tocopherol | 0.200 g | 6.0 g |
| NaOH | max 0.06 g | max. 1.8 g |
| water for injection | ad 1000 ml | ad 30.0 l |

[1] The amount of EPA and DHA is 55.5 wt.-%, based on the total amount of fatty acids in the fish oil triglyceride. The weight ratio of EPA to DHA is 3:2.

Experiments Using a Stroke Model

In order to determine the effects of the emulsion of the invention in the treatment of neurological damages after stroke the emulsions as reflected in Table 4 have been analyzed.

TABLE 4

| Components | Example 1 (Lipofundin MCT) | Example 2 (5:5 emulsion) | Example 3 (9:1 emulsion) |
|---|---|---|---|
| Soybean oil (LCT) | 100 g | — | — |
| MCT[1] | 100 g | 100 g | 20 g |
| Fish oil triglycerides[2] | — | 100 g | 180 g |
| Egg lecithin | 12 g | 12 g | 12 g |
| Glycerol | 25 g | 25 g | 25 g |
| Sodium oleate | 0.3 g | 0.3 g | 0.3 g |
| α-tocopherol | 0.2 g | 0.2 g | 0.2 g |
| NaOH | max. 0.06 g | max. 0.06 g | max. 0.06 g |
| Water for injection | ad 1000 ml | ad 1000 ml | ad 1000 ml |

[1] mid chain triglyceride
[2] the amount of EPA and DHA is 55 wt. % based on the total weight of the fatty acids in the fish oil triglyceride. The weight ratio of EPA to DHA is 3:2

The stroke model used to determine the effects of the emulsions of the invention is described in J. Dong, B. Mitkari, M. Kipp and C. Beyer Brain, Behavior, and Immunity 25 (2011) 715-726.

Method

Animals and experimental transient middle cerebral artery occlusion (+MCAO) procedure in normal Male Wistar rats Male Wistar rats (approx. 300 g, 3 months-old, Charles River, Germany) were maintained in a pathogen-free environment. Animals underwent routine cage maintenance once a week and microbiological monitoring according to the recommendations of the Federation of European Laboratory Animal Science Association.

Food and water were ad libitum. Research and animal care procedures were approved by the Review Board for the Care of Animal Subjects of the district government (Nordrhein-Westfalen, Germany). Animals were anesthetized with 5% isoflurane (Abbott, Ludwigshafen, Germany), and maintained on 1.5-2.5% isoflurane (depending on the individual animal and operation step) using a facemask. After a midline neck incision, the left common carotid artery (CCA), internal carotid artery (ICA), and external carotid artery (ECA) were exposed. Subsequently the proximal ECA and CCA were ligated. The vagus nerve was carefully preserved as far as possible. A commercially available catheter (Asahi PTCA Guide Wire Soft, Abbott Vascular, Germany) was subsequently introduced from the lumen of the distal CCA just before the bifurcation into the ICA as far as a resistance was manually observed. Thus, the origin of the middle cerebral artery (MCA) was occluded by the tip of the catheter to obtain a drop in the cerebral blood flow (CBF) by >50% compared to baseline values (see below). Body temperature was maintained at 37-37.5° C. with a heating pad and lamp during the entire surgery procedure. After one hour, the catheter was retracted and the reperfusion period initiated. Subsequently, the exposed vessels were carefully ligated to prevent bleeding, the incision closed aseptically, and the animals returned to their cages. 23 hours later, rats were deeply anesthetized with 5% isoflurane and tissue staining, molecular analysis, and animal behavioral testing were performed.

Hormone and Oil Emulsion Preparation as Well as its Application

Application of Emulsions and Blood Sampling

The emulsions as described in Table 4 were applied through a permanent jugular vein catheter 1 and 12 h after the onset of tMCAO.

For venous blood sampling and application of emulsions, the right external jugular vein was externalized by preparing from all connective tissue and fascia in the ventral neck region.

After a small incision into the vein, the tip of jugular catheter (Alzet, rat jugular catheter, Cupertina, Calif., USA) was introduced about 1-1.5 mm distally. The vein was ligated permanently 2 mm rostral and loosely distal next to the incision over the catheter. The catheter remained in position until the end of the experiment (sacrificing after 24 h).

All injections were performed at a volume of 500 µl slowly for 3 min using a micro pump system (Aesculap, Germany). To avoid coagulation of the catheters tip within the jugular vein, the tube was flooded with highly diluted heparin (1:1000 in physiological NaCl).

All used solutions were warmed-up to body temperature (38° C.) before application.

Hormones (17β-estradiol and progesterone) were prepared dissolved in 100% ethanol as stock solutions and further diluted in the provided emulsions Examples 1 to 3

Resulting dosage of steroids per application was:
Progesterone (P, Sigma-Aldrich, Germany) 10 mg/kg body weight
17β-Estradiol (E, Sigma-Aldrich, Germany) 25 µg/kg body weight Emulsions with or without hormones were applied 1 h and 12 h after the onset of tMCAO.

Additionally to the emulsions, a lipid free hormone containing sodium chloride/ethanol solution was prepared (NaCl/EtOH E/P). Again, a stock solution was prepared by dissolving the hormones in ethanol. Further dilution of the stock solution in saline (NaCl) resulted in same application volume (500 µl) and dosage regime as shown above for the emulsions.

Assessment of Regional Cerebral Blood Flow (rCBF)

To assure an appropriate MCA occlusion, a Laser-Doppler flowmetry (LDF) to measure regional cerebral perfusion over the MCA during focal cerebral ischemia was used.

Therefore, each animal underwent craniotomy for placement of a 2-mm laser-Dopplerprobe (PeriFlux System 5000, Type PF 5001, Perimed, Sweden) over the intact dura mater at approximately 3-5 mm posterior to bregma and 4 mm lateral to midline. Baseline measurements were taken directly before insertion of the catheter into the ICA. rCBF over the MCA was recorded in 10 minute intervals and the mean was calculated. Only animals with a reduction of rCBF by at least 50% (mean value) compared to the baseline were further included in the study. The other animals were excluded from the study, since no appropriate oxygen undersupply/infarction could be guaranteed.

Analysis of Animals

Generally, all analysis was performed in a single-blinded manner. In this context, single-blinded means that the first experimenter who performed preparation of applied emulsions, tMCAO surgery, and the application of all emulsions was aware of the tested drugs. This person then encoded the animals with numbers. The second experimenter who handled behavioral testing, analysis of stroke volume analysis was completely blinded and only handled animals labeled with a coded number. This person then made the analysis and mathematical/statistical evaluations and returned data set to the first experimenter who was assigning the data to the corresponding animals/treatments.

Measurement of the Infarct Volume

The data of infarct volume are expressed as percentage changes compared to the total infarct volume in unprotected tMCAO animals which was always set to 100%. This allows to a better comparing the levels of protection at a glance.

For the exact evaluation of the infarct volume, the 2,3,5-triphenyltetrazolium chloride (TTC) staining method was applied. Brains were rapidly dissected out and cut into 2-mm thick coronal sections using a rat brain matrix (Alto Brain Matrix stainless steel 1 mm rat coronal 300-600 GM, Havard-Apparatus). Sections were then incubated in a 2% TTC solution (prepared in saline) at 37° C. for 15 min. Living tissue stains red, while the infarcted tissue does not stain and remains pale. After TCC staining, the sections were cryo-preserved. The images of the TTC-stained sections were acquired with a Canon Digital IXUS 9015 camera. Total cortical infarct volume was calculated by adding the mean-area of each section and multiplied by 2 mm (thickness of the sections). Edema correction of infarct volume was done using the equation, volume correction (cortical infarct volume×entire contralateral volume)/entire ipsilateral volume. The edema volume was calculated by subtracting the volume of the ipsilateral lesioned from the contralateral hemisphere (Garcia et al. *Stroke* 26:627-634, 1995). Measurements were performed using a free-accessible software device (Image) 1.41, USA).

Behavioral Testing

Briefly before scarifying animals, behavioral tests (Garcia Neuroscoring) were performed with all rats included in the study according to Garcia et al. (*Stroke* 26:627-634, 1995) with minor modifications. Six independent behavioral tests which were scored from 1-3 resulting in a maximum of 18 scores were performed. The following behaviors have been assessed: Spontaneous activity, forepaw outstretching, and ability to climb, body proprioception with blunt stick), body proprioception (vibrissae touching), spontaneous walking. Typically, intact or sham-operated animals always scored 18 P. In contrast, tMCAO animals scored in average approx. 6 P.

Figure 2:
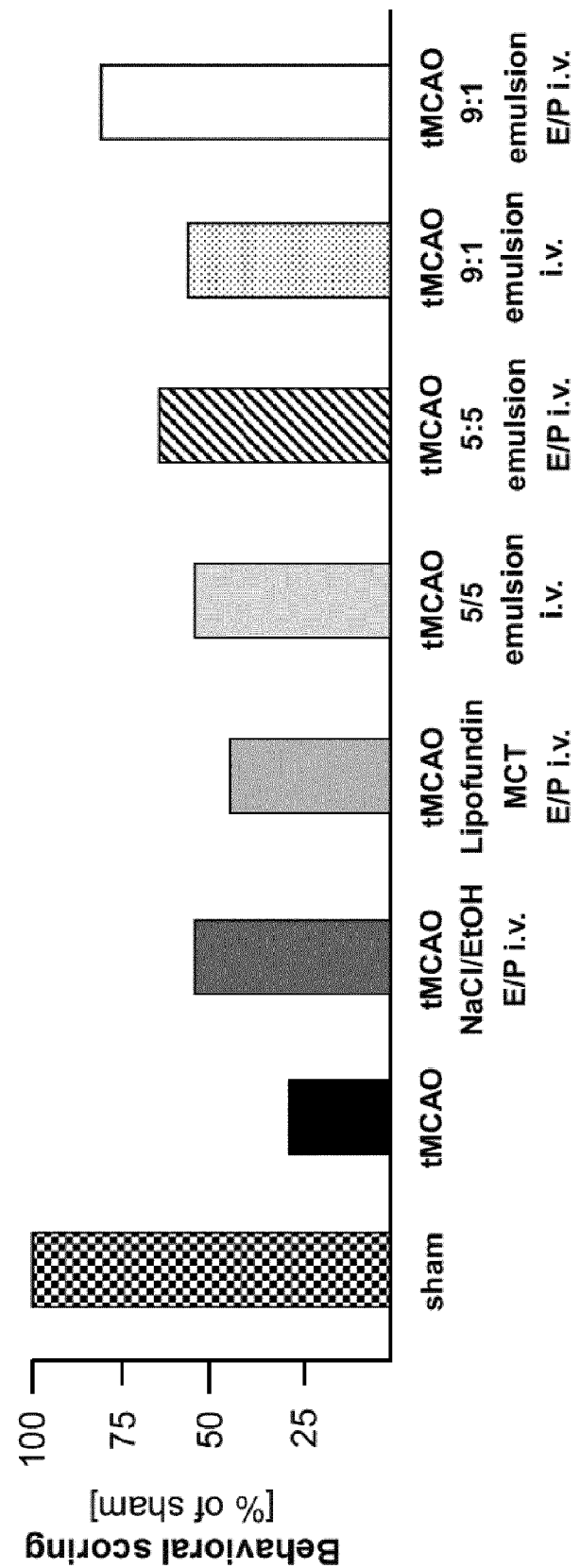

The results of the tests with the stroke model are reflected in FIGS. 1 and 2.

In the Figures the following abbreviations have been used:

NaCl/EtOH E/P i.v.: Hormone containing sodium chloride/ethanol solution as described above which is intravenously administered Lipofundin MCT E/P i.v.: Emulsion according to Example 1 in Table 4 with hormones added as described above and intravenously administered 5/5 emulsion i.v.: Emulsion according to Example 2 without hormones and intravenously administered 5:5 emulsion E/P i.v.: Emulsion according to Example 2 in Table 4 with added hormones as described above and intravenously administered 9:1 emulsion i.v.: Emulsion according to Example 3 without hormones and intravenously administered 9:1 emulsion E/P i.v.: Emulsion according to Example 3 in Table 4 with added hormones and intravenously administered FIG. 1 demonstrates the effect of treatment on the volume of the cerebral cortex infarct volume.

FIG. 2 demonstrates the effect of treatment on behavioral scoring.

As can be seen from the results the use of the omega-3 fatty acid rich fish oil emulsions (Examples 2 and 3) together with the hormones progestogen and estrogen demonstrates a synergistic and unexpected improved effect.

The invention claimed is:

1. A hormone containing oil-in-water emulsion for parenteral administration, wherein an oil component of the oil-in-water emulsion comprises
    a) progestogen and/or estrogen;
    b) fish oil triglycerides, wherein the fish oil triglycerides consist of glycerol which is esterified with fatty acids wherein said fatty acids comprise eicosapentaenoic acid (EPA) and docosahexaenoic acid (DHA) in an amount of at least 45% by weight of said fatty acids, wherein the fish oil triglycerides are present in an amount ranging from 70 wt. % to 95 wt. % based on the total weight of the oil component; and
    c) medium chain triglycerides (MCT), where the MCT are present in an amount ranging from 5 wt. % to 30 wt. % based on the total weight of the oil component.

2. A hormone containing oil-in-water emulsion according to claim 1, wherein the emulsion comprises progestogen and estrogen in a weight ratio of 2:1 to 500:1.

3. A hormone containing oil-in-water emulsion according to claim 1, wherein the emulsion comprises estradiol and/or progesterone.

4. A hormone containing oil-in-water emulsion according to claim 1, wherein the emulsion comprises progesterone in an amount ranging from 0.15 to 12 g/l and/or the emulsion comprises estradiol in an amount ranging from 0.015 g/l to 1.5 g/l.

5. A hormone containing oil-in-water emulsion according to claim 1, wherein the fish oil triglyceride consists of glycerol which is esterified with fatty acids wherein the total amount of omega-3-fatty acids is at least 50 wt. % based on the total amount of esterified fatty acids.

6. A hormone containing oil-in-water emulsion according to claim 1, wherein the emulsion comprises an emulsifier selected from the group consisting of egg lecithin, soya lecithin, phospholipids derived from marine crustacean and mixtures thereof.

7. A hormone containing oil-in-water emulsion according to claim 1, wherein the emulsion comprises phospholipids comprising omega-3-fatty acid moieties.

8. A hormone containing oil-in-water emulsion according to claim 1, wherein the emulsion comprises 1 g/l to 2 g/l of progesterone, 0.05 g/l to 1.0 g/l of estradiol, 100 g/l to 300 g/l of oil, 4 to 20 g/l of a phospholipid, and 10 to 50 g/l of glycerol.

9. A hormone containing oil-in-water emulsion according to claim 1, wherein the emulsion comprises less than 10 wt. % of vegetable oils.

10. A method of treating neurological damage after a stroke and/or trauma, the method comprising delivering the emulsion according to claim 1 to a patient, wherein the patient has suffered a stroke or a traumatic brain injury.

11. A method of treating neurological damage after a concussion or as a result of a traumatic event, the method comprising delivering the emulsion according to claim 1 to a patient, wherein the patient has suffered a concussion or other traumatic event.

* * * * *